United States Patent [19]

Hershman et al.

[11] B 4,001,213

[45] Jan. 4, 1977

[54] REPRESSION OF POLYMER FORMATION IN THE CONVERSION OF LINEAR OR BRANCHED PRIMARY DIAMINES TO CYCLIC IMINES

[75] Inventors: Arnold Hershman, St. Louis, Mo.; Anthony J. C. Pearson, Highton, Australia

[73] Assignee: Monsanto Company, St. Louis, Mo.

[22] Filed: May 17, 1974

[21] Appl. No.: 470,900

[44] Published under the second Trial Voluntary Protest Program on March 2, 1976 as document No. B 470,900.

Related U.S. Application Data

[63] Continuation-in-part of Ser. No. 26,131, April 6, 1970, abandoned.

[52] U.S. Cl. .................. 260/239 B; 260/239 A; 260/293.51; 260/326.8
[51] Int. Cl.$^2$ ............ C07D 207/06; C07D 211/02; C07D 223/04; C07D 295/02
[58] Field of Search ........ 260/239 A, 239 B, 326.8, 260/293.51, 268 SY

[56] References Cited

UNITED STATES PATENTS

| | | | |
|---|---|---|---|
| 2,200,282 | 5/1940 | Lazier | 260/239 B |
| 2,267,686 | 12/1941 | Kyrides | 260/268 SY |
| 2,863,872 | 12/1958 | Silverstone | 260/326.8 |
| 2,952,688 | 9/1960 | Kline et al. | 260/313 |
| 3,268,588 | 8/1966 | Horlenko | 260/239 B |

FOREIGN PATENTS OR APPLICATIONS

| | | | |
|---|---|---|---|
| 892,034 | 3/1943 | France | 260/239 B |
| 738,448 | 8/1943 | Germany | 260/239 B |

OTHER PUBLICATIONS

Yasumura, Chem. Abstracts, vol. 59, Col. 2813 (1963).

*Primary Examiner*—Alton D. Rollins

[57] ABSTRACT

The conversion of linear or branched primary diamines to saturated secondary cyclic amines with the repression of the formation of linear or branched secondary amines, tertiary amines and polymers is carried out in the vapor phase, with a diluent, preferably hydrogen, over a solid catalyst comprising an element selected from the group consisting of nickel, copper, cobalt or iron.

16 Claims, No Drawings

REPRESSION OF POLYMER FORMATION IN THE CONVERSION OF LINEAR OR BRANCHED PRIMARY DIAMINES TO CYCLIC IMINES

SUMMARY OF THE INVENTION

This application is a continuation-in-part of Ser. No. 26,131 filed on Apr. 6, 1970, and now abandoned.

In order to reduce the formation of linear or branched secondary amines, tertiary amines and polymers in the conversion of linear or branched primary diamines to form saturated cyclic secondary amines (hereinafter sometimes called cyclic imines) the reaction of the present invention is carried out in the substantial absence of ammonia, but with an atmosphere of an inert gas such as nitrogen or preferably hydrogen at a temperature of from 100°C to 250°C at relatively low pressures, e.g., preferably 115 p.s.i.a., to vacuum conditions. The reaction is carried out in the vapor phase, which has been found to greatly reduce the formation of polymeric byproducts such as are formed in a liquid phase reaction. The use of a diluent in the vapor phase leads to enhanced selectivity to the cyclic imines. Preferred molar ratios of the diluent, preferably hydrogen, to diamine are 0.1:1 to 50:1 with a more preferred range being 2:1 to 25:1. The solid catalyst employed for the present vapor phase reaction is comprised of an element selected from the group nickel, copper, cobalt or iron or mixtures thereof. The catalytic species may also be charged as a compound such as the oxide which under reaction conditions is at least partly reduced to the elemental metal.

BACKGROUND OF THE INVENTION

The formation of amines for example by the catalytic hydrogenation of nitriles in the presence of excess ammonia is well known. However the conversion of linear or branched primary diamines to cyclic imines is a more difficult procedure, particularly since the starting amines readily form higher amine compounds such as, e.g., secondary amines and tertiary amines with the result that a considerable proportion of the starting amines are lost as polymeric products.

Most of the prior art employs the liquid phase. However, Raab (German Pat. No. 738,448) teaches the conversion of 1,6 diaminohexane to perhydroazepine. The reaction is carried out in the gas phase over catalysts such as chromium or vanadium oxides. Temperatures of 300°–450°C are taught. This temperature range is much higher than has been found to be necessary with the metal catalysts claimed herein. In fact none of the prior art combines the particular catalysts, employed under the conditions of temperature, vapor phase reaction and preference for a hydrogen diluent taught herein. As shown in the examples this unique combination leads to unexpectedly high selectivity to saturated cyclic secondary amines while repressing the formation of linear or branched secondary amines, tertiary amines and other higher polymers. When a liquid phase reaction is conducted, significant quantities of heavy, worthless, polymeric residues are formed. Other metals such as rhodium and palladium give much poorer selevtivity to the cyclic imine. The use of hydrogen as a preferred vapor phase diluent is also not anticipated in the prior art. Hydrogen surprisingly plays a unique role beyond that of a diluent in producing the superior selectivity to cyclic imine (i. e. saturated cyclic secondary amine) claimed herein.

DESCRIPTION OF THE PREFERRED EMBODIMENTS

The diamines employed as feedstocks in the present process have a carbon chain of from 3 to 7 atoms between the amine groups with a carbon chain of 5 or 6 atoms between the amine group being preferred.

The feedstock is vaporized and passed over the solid catalyst in the vapor phase, preferably with the employment of a diluent atmosphere of hydrogen. Other inert gas such as nitrogen, carbon monoxide, methane, argon, helium, etc., or mixtures thereof may also be employed but the formation of polymer is not suppressed as much as when hydrogen is employed. It has been found that the use of added ammonia which is conventional in the selective hydrogenation of nitriles to amines is highly undersirable in the present reaction. In fact it has been discovered that the presence of significant proportions of added ammonia deleteriously affects not only the rate but the selectivity of the reaction to cyclic imines. Suitable feedstocks include 1,3-propanediamine, 1,4-butanediamine 1,7-heptanediamine, 1,5-pentane-diamine and 1,6-hexanediamine with the latter two being preferred feedstocks. Substituted feedstocks having methyl, ethyl and phenyl substituents along the carbon chain may also be employed. A preferred diamine feedstock for which unusually high selectivity can be achieved have a carbon chain of 5 or 6 carbon atoms between amine groups.

Typical starting materials and ultimate products of the present invention are shown in Table I below. It has been found that the present temperatures of 100°C to 250°C are desirable with respect to the prevention of yield losses due to side reactions. Higher temperatures, e.g., 400°C result in cracking and the formation of unwanted lower boiling fractions.

A diluent gaseous carrier such as hydrogen is employed to increase selectivity and suppress polymer formation. The preferred mole ratio of diluent, such as hydrogen, relative to diamine feed lies within the range 0.1:1 to 50:1. A more preferred range is 2:1 to 25:1. Other inert gases such as nitrogen, methane (or natural gas) or other inert gaseous mixtures thereof may also be employed at the above ratios but the results are not as good as when hydrogen is employed.

TABLE I

| Starting Material | Saturated Cyclic Secondary Amine Products (Cyclic Imines) | Structure |
|---|---|---|
| 1,3-diamino propane | azetidine | CH₂⟨CH₂-CH₂⟩N-H |
| 2,4-diamino pentane | 2,4-dimethylazetidine | H₃C—CH⟨CH₂-CH₂—CH₃⟩NH |

TABLE I-continued

| Starting Material | Saturated Cyclic Secondary Amine Products (Cyclic Imines) | Structure |
|---|---|---|
| Putrescine | pyrrolidine | (structure shown) |
| 2,5-diamino hexane | 2,5-dimethylpyrrolidine | (structure shown) |
| 3,6-diamino octane | 2,5-diethyl pyrolidene | (structure shown) |
| cadaverine (1,5-diamino pentane) (Preferred feedstock) | piperidine (perhydroazine) | (structure shown) |
| 2,6-diamino heptane (Preferred feedstock) | 2,6-dimethylpiperidine | (structure shown) |
| 1,6-diamino hexane (hexamethylenediamine) (preferred feedstock) | perhydroazepine (hexamethylene imine) | (structure shown) |
| 2,7-diamino octane | 2,7-dimethyl perhydroazepine | (structure shown) |
| 1,7-diamino heptane | perhydroazocine | (structure shown) |

The reaction is conducted with a solid catalyst which is disposed in a tube or on trays in a cylindrical reactor through which the reactant mixture is passed. The reactor may consist of a series of catalyst beds with optional interstage cooling between the beds or the catalyst may be placed in these with a heat exchange medium around the tubes. The tubes containing the catalyst may be run in parallel or in series. The metal content of the catalyst may be varied through the reactor to provide operating advantages. A bed of the catalyst support, per se, without metal components may also be used so that the gas stream passes through such a bed in order to pick up any catalyst swept out of the reactor. It is also an embodiment of the invention of use either upflow or downflow of the reactants through the reactor, with periodic reversal of the gas stream also being contemplated to provide operating advantages such as maintaining a clean catalyst bed.

A fluid bed reactor may also be employed if desired. In such a case it may be advantageous to remove catalyst for regeneration with consequent replacement in a batch, semicontinuous or continuous basis.

Some catalysts may require periodic regeneration to maintain their effectiveness. This invention is not limited to nonregenerable catalysts. Hence if desired said catalysts may be regenerated by treatment with hydrogen at elevated temperatures, treatment with air followed by treatment with hydrogen or other means known by those skilled in the art.

The catalyst employed in the present vapor phase reaction comprises a metal component, preferably dispersed upon a carrier. The elemental metal such as nickel or copper may be employed in massive form or preferably as a dispersed form of the metal as a salt such as nickel nitrate, copper nitrate, etc., on a carrier such as alumina or kieselguhr, followed by thermal decomposition or calcination of the metal compound and reduction to the dispersed elemental metal.

The metals which are of utility in the present invention are selected from the group consisting of nickel, copper, cobalt and iron. The metals may also exist as ligands, together with inorganic and organic ligands disposed upon a carrier for example pentacyanocobalt on alumina. These four metals give superior selectivity to the cyclic imines versus other metals. This is surprising since other Group VIII metals such as the noble metals e.g. rhodium, palladium, platinum also catalyze the cyclization reaction. Not only are these noble metals much more expensive but, as shown in the examples, they do not give the remarkably specific reaction of the diamine to the saturated cyclic secondary amine with repression of polymeric byproducts.

The following examples show specific embodiments of the present invention.

EXAMPLE 1

A solid supported catalyst containing a nickel component dispersed upon an alumina catalyst support is prepared by a minimum solution technique in the following manner: An amount of 13.76 gm of nickel nitrate hexahydrate, having the formula $Ni(NO_3)_2.6H_2O$, is dissolved in 12.5 gm water. The resulting solution is stirred together with 25 gm of an activated alumina (Kaiser Aluminum Corp.) and this mixture is dried at 125°C in an oven. The dried impregnated alumina is then charged into a 1 inch diameter pyrex tube which is situated in a thermostatically controlled tube furnace. A thermocouple in a glass thermowell is positioned at the mid point of the catalyst in order that the catalyst temperature may be monitored. A stream of air is passed over the catalyst and the temperature in the tube raised to 500°C over two hours and held at that temperature for a further two hours. The system is then purged with helium and cooled to 150°C. At this point sufficient hydrogen is introduced into the helium stream to form a mixture of 5% hydrogen in helium and the catalyst temperature is again raised to 500°C over 2 hours. On reaching 500°C the hydrogen content of the gas stream flowing through the catalyst is gradually raised to 100% and these conditions once maintained for a period of 3 hours. The tube containing the now reduced nickel on alumina catalyst is removed from the furnace and cooled to room temperature and kept sealed to prevent the entry of air.

Ten ml of the above supported catalyst is then charged (under an inert atmosphere of nitrogen) into an 24 inch pyrex tube having an outside diameter of ¾ inch. The resulting catalyst bed, 5 cm in depth is supported above and below by inert beds of Vycor glass rings. The tube is positioned vertically in a temperature controlled furnace. There is a central thermowell and thermocouple in the reactor tube to enable the catalyst temperature profile to be measured. The process is conducted in the vapor phase at a liquid hourly space velocity (LHSV) of 0.2 of 1,6-diamino hexane using a hydrogen diluent at a molar ratio $H_2/H_2N(CH_2)_6NH_2$ of 20. The pressure at which the gaseous reactants contact the supported catalyst is 1 atmosphere, at a reaction temperature of 150°C.

The reactor effluent is condensed using a chilled water condenser in train with a cold finger condenser cooled by dry ice/acetone. A gas chromatographic analysis (GC) of the condensed product indicates a conversion of 1,6-diamino hexane of 100% and a selectivity to perhydroazepine of 80%.

Polymer levels if present are at such low levels that they are below the level of detection of the chromatographic detector (less than 0.1%). That such an excellent selectivity to perhydroazepine is achieved at total conversion of the 1,6-diaminohexane is quite unexpected particularly with the essentially total repression of polymer (the gas chromatography analysis employs a very sensitive flame ionization detector so polymer formation is easily detectable). At comparable conditions employing a supported nickel catalyst but with the 1,6 diaminohexane in the liquid phase considerable polymer formation occurs. Recognizing the role of dilution in minimizing polymer formation in the liquid phase, an ethanol diluent is employed so that the 1,6 diaminohexane is only present as a 20% solution in the ethanol. Ethanol is a true inert diluent, since gas chromatographic (GC) analysis of the liquid solution at the end of the reaction shows that ethanol goes through the reaction unchanged and no ethanol by-products are formed. At 125°C and 400 psi $H_2$ the liquid phase reaction product after 17 hours employing the supported nickel catalyst analyzed by GC as 73% conversion with 79% selectivity to perhydroazepine and 11% by-product loss to polymeric material.

The comparison of the liquid and vapor phase result is presented below for the supported nickel catalyst:

| Phase in which Reaction Conducted | Conversion of 1,6-diamino-hexane | Selectivity to Perhydro-azepine | By-product loss to Polymer |
| --- | --- | --- | --- |
| Vapor | 100% | 80% | <0.1% |
| Liquid | 73% | 79% | 11% |

EXAMPLE 2

A commercially prepared supported nickel catalyst is employed in a vapor phase reaction system at several different operating conditions with very high selectivity to perhydroazepine and with repression of polymer formation. The catalyst employed is Girdler G49B, 55% Ni on Kieselguhr. At 175°C with a LHSV of 0.23 and a hydrogen to diamine molar ratio of 14 the conversion of 1,6 diaminohexane is 100%, the selectivity to perhydroazepine is 96% and polymer formation is below the level of detection by GC (less than 0.1%). At 150°C with a LHSV of 0.2 and a hydrogen to diamine molar ratio of 20 the conversion is 100% and selectivity is 90% again with no detectable polymer formation.

Hydrogen is a preferred gaseous carrier with the most preferred range of hydrogen to diamine molar ratio being 2:1 to 25:1. At these hydrogen ratios in the vapor phase long term catalyst activity is achieved, at very high conversion, very high selectivity and with repression of polymeric by-products formed in a liquid phase reaction employing the same diamine feed and catalyst.

EXAMPLE 3

A commercial supported copper catalyst, Girdler T366, which is 55% Cu on Kieselguhr is employed in the vapor phase reactor described in Example 1. The diamine reactant is 1,6 diaminohexane and the operating conditions are: temperature 150°C, LHSV 0.1 and hydrogen to diamine molar ratio of 20. As with the nickel catalysts of Examples 1 and 2 an excellent result is achieved. The conversion of diamine is 100% with selectivity to perhydroazepine of 95% and no polymer is detected by GC analysis (less than 0.1%).

EXAMPLE 4

Cobalt and iron catalysts also are excellent catalysts for the formation of cyclic imines from diamines in the vapor phase with repression of polymeric by-products. A 15% cobalt on alumina catalyst employing the vapor phase reactor system of Example 1 gives 81% selectivity to perhydroazepine with no detectable level of polymeric by-products.

When a supported cobalt catalyst is employed in a liquid phase reaction system at comparable operating conditions 63% of the 1,6-diaminohexane is converted to polymer by-products and only 32% selectivity to perhydroazepine is achieved. Ethanol is employed as the inert diluent in the liquid phase reaction system and GC analysis confirms that ethanol behaves as an inert to the system. The polymeric material which forms is built up from 1,6 diaminohexane and the perhydroazepine segments.

The comparison of the results for the vapor phase versus the liquid phase reaction with a cobalt catalyst is presented below:

| Phase of Reaction | Selectivity to Perhydroazepine | By-product loss to Polymer |
|---|---|---|
| Vapor | 81% | <0.1% |
| Liquid | 32% | 63% |

EXAMPLE 5

Other metals also catalyze the vapor phase cyclization of diamines to cyclic imines but without the selectivity of the iron subgroup (i.e. Fe, Co, Ni) and copper. At 150°C, a LHSV of 0.2 and a hydrogen to 1,6 diaminohexane molar ratio of 20 and employing the vapor phase reactor described in Experiment 1 a 5% rhodium on alumina catalyst only gives a selectivity to perhydroazepine of 15% at 100% conversion of the diamine.

EXAMPLE 6

Similarly the addition of palladium to cobalt gives a catalyst with poorer selectivity than with cobalt alone as the metal component of the catalyst. At 150°C, a LHSV of 0.3 and a hydrogen to 1,6 diaminohexane molar ratio of 20 the selectivity to perhydroazepine is only 47%. In Example 4 a cobalt catalyst gives a selectivity of 81%. While palladium increases the activity of the catalyst system it drastically reduces the selectivity to the desired cyclic imine product.

EXAMPLE 7

A chromia-alumina catalyst is described in Raab (German Pat. No. 738,448) for the vapor phase conversion of diamines to cyclic imines. However the temperatures employed by Raab as shown in the examples of his patent are 300°–380°C, significantly higher than those found to be effective for high selectivity and repression of polymer employing Ni, Cu, Co and Fe as catalysts. To determine the performance of Raab's chromia alumina catalyst at our operating temperatures a similar experiment to Experiment 1 is conducted except employing a commercial chromia-alumina catalyst (Harshaw CR-0205T). This catalyst contains 19% $Cr_2O_3$ on activated alumina, and is comparable to the 10% metalic nickel loading of Experiment 1. The experiment is conducted at the same temperature (150°C), liquid hourly space velocity (0.2) and mole ratio of hydrogen to 1,6 diaminohexane (20) as in Experiment 1.

When operating with the chromia-alumina at this temperature, there is no conversion (i.e. 0% yield and 0% selectivity). The temperature then is raised as high as 250°C without any detection of conversion or selectivity to cyclic imine products in the reactor effluent as set forth above. In contrast, the nickel on alumina gave 100% conversion and 80% selectivity to cyclic imine. The results for Experiments 1 through 7 are summarized in Table II below. These results clearly demonstrate the superior results for the catalysts comprising an element selected from the group consisting of nickel, copper, cobalt and iron.

TABLE II

| Example No. | Catalyst | LHSV | Molar Ratio $H_2$/Diamine | Selectivity to Perhydroazepine, mole% | Polymer By-product, mole% |
|---|---|---|---|---|---|
| Reactant | | 1,6 diaminohexane | | | |
| Operating Conditions: | | 150°C, atmospheric pressure | | | |
| | Claimed Metal Catalysts | | | | |
| 1 | 10% Ni/KA101 alumina | 0.2 | 20 | 80 | <0.1 |
| 2 | Girdler G49B 55%Ni/Kieselguhr | 0.23[a] | 14 | 96 | <0.1 |
| | | 0.2 | 20 | 90 | <0.1 |
| 3 | Girdler T366 55%Cu/Kieselguhr | 0.1 | 20 | 95 | <0.1 |
| 4 | 15% Co/KA101 alumina | 0.2 | 20 | 81 | <0.1 |
| | Other Metal Catalysts | | | | |
| 5 | 5% Rh/Alumina | 0.2 | 20 | 15 | [b] |
| 6 | 5% Pd,5%Co on silica gel | 0.3 | 20 | 47 | [b] |
| 7 | Harshaw Cr 0205T 19%$Cr_2O_3$ on alumina | 0.2 | 20 | 0[c] | — |

[a]Operating temperature 175°C
[b]Not analyzed by GC for polymer
[c]0% conversion even at 250°C

EXAMPLE 8

The catalyst of Example 2, 55% Ni on Kieselguhr, is employed in a vapor phase catalyst system at the same temperature and LHSV as in Example 2 (150°C, LHSV = 0.2). The component of the gaseous diluent, however, is varied. The results are tabulated below:

| Mole Ratio Diluent/1,6 diaminohexane | | | Conversion | Selectivity to Perhydroazepine |
| --- | --- | --- | --- | --- |
| $H_2$ | $N_2$ | $NH_3$ | | |
| 20 | | | 100 | 90 |
| | 20 | | 70 | 57 |
| 6 | | 14 | 62 | 45 |

The results above clearly show that hydrogen is a preferred gaseous diluent for the vapor phase cyclization of diamines to cyclic imines. It can be seen that nitrogen, while useful, is not as effective a diluent as hydrogen since nitrogen gives poorer conversion and selectivity. It is quite unexpected that hydrogen should produce a far superior result to nitrogen as a diluent. The deleterious affect of ammonia is expected. Since ammonia is a product of the cyclization, the decrease in conversion from 100% to 62% is not unreasonable. It is surprising however that the selectivity to perhydroazepine is reduced more than 50% in the presence of ammonia versus hydrogen as the gaseous diluent.

EXAMPLE 9

When 1,5-diamino pentane is passed in the vapor phase over a commercial 55% nickel on Kieselguhr catalyst at an LHSV of 0.2 at mole ratio $H_2:H_2N(CH_2)_3NH_2$ of 10 at a catalyst bed temperature of 175°C, substantiatly 100% conversion of the 1,5-diamino pentane is achieved, with a selectivity of better than 95% to piperidine.

EXAMPLE 10

A catalyst as described in Example 1 is prepared and 10 cm³ are charged to the reactor and its temperature raised to 150°C under a flow of hydrogen. When a feed of 2,7-diamino octane is passed in the vapor phase over the catalyst at LHSV 0.20 at mole ratio $H_2$:2,7-diamino hexane of 20, a conversion of 97% of the diamine fed at a selectivity of 94% to 2,7-dimethyl perhydroazepine is achieved.

Examples 9 and 10 demonstrate that comparable excellent results to those for the cyclization of 1,6-diaminohexane are achieved for feedstocks with 5 carbons between the amine groups and for feedstocks with 6 carbons between amine groups but with additional groups on the carbon atoms which are between the amine groups. Examples 11-13 are for diamine feeds having 3,4 or 7 carbon atoms between the amine groups. The conversion and selectivity achieved is lower than for the examples using a diame feed with 5 and 6 carbon atoms between the amine groups. Clearly the preferred diamine configuration for cyclization with the catalyst systems claimed herein is 5 or 6 atoms between the amine groups.

EXAMPLE 11

When 1,7-diamino heptane is passed in the vapor phase over a commercial 55% copper on Kieselguhr catalyst in the apparatus described in Example 1 at an LHSV of 0.1, using a hydrogen diluent at mole ration $H_2:H_2N(CH_2)_7NH_2$ of 20 at 150°C, the conversion of the 1,7-diamino heptane feed is only 10%. When the catalyst temperature is raised to 175°C a conversion of 15% with selectivity of 70% to the desired perhydroazocine is achieved.

EXAMPLE 12

A catalyst as described in Example 2 is charged to the reactor and its temperature raised to 150°C under a flow of hydrogen. When a feed of 1,3-diamino propane is passed over the catalyst at LHSV 0.4 at mole ratio $H_2:H_2N(CH_2)_3NH_2$ of 15 a conversion of the feed of 10% at high selectivity to azetidine results.

EXAMPLE 13

A catalyst as described in Example 1 is prepared and charged to the reactor and its temperature raised to 175°C under a flow of hydrogen. When a feed of 1,4-diamino butane is passed over the catalyst at LHSV 0.15 at mole ratio $H_2:H_2N(CH_2)_4NH_2$ of 14.5 all but trace amounts of the 1,4-diamino butane is converted, with a selectivity much greater than that achieved when 1,4-diamino butane is cyclized in a liquid phase reaction.

What is claimed is:

1. Process for the conversion of linear or branched primary alkyl diamines to saturated cyclic secondary amines, the said diamines having a carbon chain of 3 to 7 carbon atoms between amine groups, with the repression of the formation of linear or branched secondary amines, tertiary amines and polymers, which comprises passing the said diamines in the vapor phase, in the absence of added ammonia, at a temperature of from 100°C to 250°C over a solid catalyst comprising an element selected from the group consisting of nickel, copper, cobalt or iron.

2. Process for the conversion of linear or branched primary alkyl diamines to saturated cyclic secondary amines, the said diamines having a carbon chain of 5 to 6 carbon atoms between amine groups, with the repression of the formation of linear or branched secondary amines, tertiary amines and polymers, which comprises passing the said diamines in the vapor phase, in the absence of added ammonia, at a temperature of from 100°C to 250°C over a solid catalyst comprising an element selected from the group consisting of nickel, copper, cobalt or iron.

3. Process for the conversion of linear or branched primary alkyl diamines to saturated cyclic secondary amines, the said diamines having a carbon chain of 3 to 7 carbon atoms between amine groups with a repression of the formation of linear or branched secondary amines, tertiary amines and polymers, which comprises passing the said diamines in the vapor phase, in the absence of added ammonia, at a temperature of from 100°C to 250°C over a solid catalyst comprising an element selected from the group consisting of nickel, copper, cobalt or iron dispersed upon a solid carrier.

4. Process as in claim 1 in which the diamine is contacted with the catalyst in the presence of hydrogen or nitrogen as a gaseous diluent.

5. A process as in claim 4 in which the said gaseous diluent is in the molar ratio of from 0.1:1 to 50:1, relative to the said diamine.

6. A process as in claim 4 in which the said gaseous diluent is in the molar ratio of from 2:1 to 25:1, relative to the said diamine.

7. Process as in claim 4 in which the said gaseous diluent is hydrogen.

8. Process as in claim 4 in which the said gaseous diluent is hydrogen and in which the said hydrogen is in the molar ratio of from 0.1:1 to 50:1, relative to the said diamine.

9. Process as in claim 4 in which the said gaseous diluent is hydrogen and in which the said hydrogen is in the molar ratio of from 2:1 to 25:1, relative to the said diamine.

10. Process as in claim 1 in which the said catalyst is nickel.

11. Process as in claim 1 in which the said catalyst is copper.

12. Process as in claim 1 in which the said catalyst is cobalt.

13. Process as in claim 1 in which the said catalyst is iron.

14. Process as in claim 1 in which the diamine is 1,6-diamino hexane and the saturated cyclic secondary amine which is obtained is perhydroazepine.

15. Process as in claim 1 in which the diamine is 1,5-diamino pentane and the cyclic secondary amine which is obtained is piperidine.

16. Process as in claim 1 in which the diamine is 2,7-diamino octane and the cyclic secondary amine which is obtained is 2,7-dimethyl perhydroazepine.

* * * * *